United States Patent [19]

Mautoni

[11] Patent Number: 5,895,367
[45] Date of Patent: Apr. 20, 1999

[54] MEDICAL THERAPEUTIC DEVICE FOR PLACING A PATIENT INTO EITHER TRACTION OR COMPRESSION

[76] Inventor: Milton Mautoni, Rua Aida, N° 30, 09850-200-Sao Bernardo Do Campo, SP, Brazil

[21] Appl. No.: 08/842,090

[22] Filed: Apr. 28, 1997

[51] Int. Cl.$^6$ ................................................. A61F 5/00
[52] U.S. Cl. .............................. 602/32; 602/33; 602/36
[58] Field of Search ............................ 602/32, 33, 34, 602/35, 36, 38; 606/241, 242; 601/33

[56] References Cited

U.S. PATENT DOCUMENTS

| | | | |
|---|---|---|---|
| 1,188,711 | 6/1916 | Wilting | 602/36 |
| 1,936,363 | 11/1933 | Murray | 606/242 |

Primary Examiner—Richard J. Apley
Assistant Examiner—Denise Pothier
Attorney, Agent, or Firm—James Ray & Associates

[57] ABSTRACT

Medical therapeutic equipment for applying tension or compression to various body parts of a patient, the equipment being a rectangular frame structure made up of a plurality tubular elements intended to be placed around the patient lying on a horizontal surface, the rectangular frame structure having an elongated post member with a ring at the end thereof in a generally parallel relationship intended to extend between the legs of the patient, and a pair of anchorage devices, a first adapted to fasten a first selected body part of the patient to the ring, and a second adapted to fasten a second selected body part of the patient to a transverse end member opposite the elongated post member, and further including an apparatus for mechanically drawing the post member and ring away from the opposed transverse end member to activate the equipment.

1 Claim, 5 Drawing Sheets

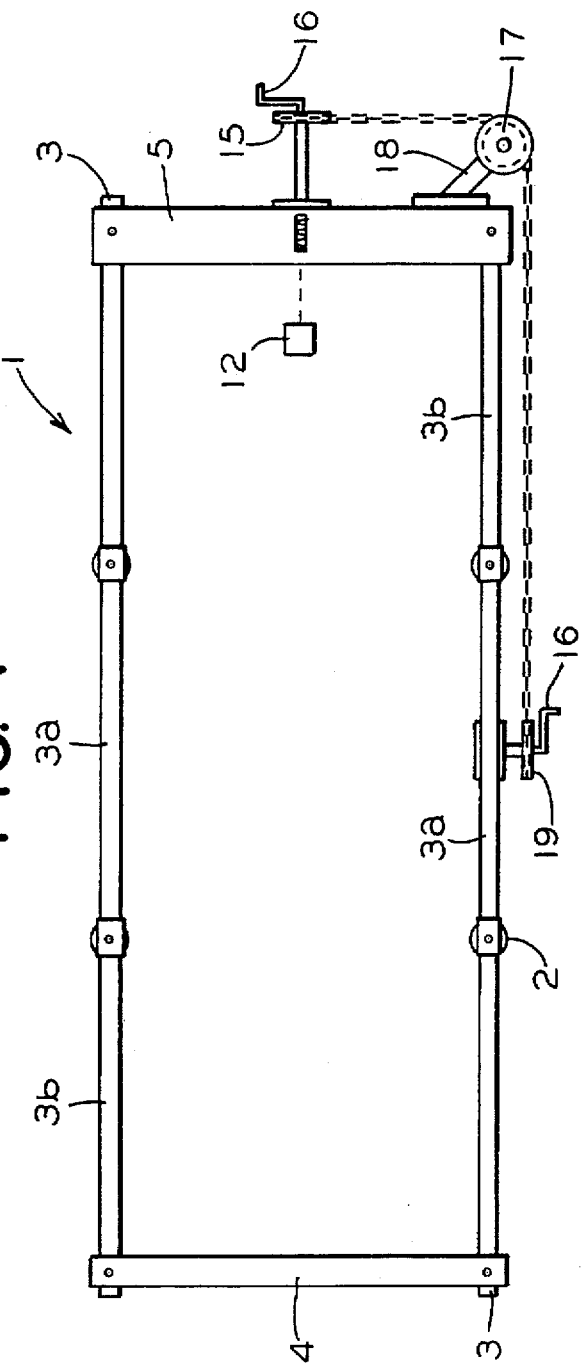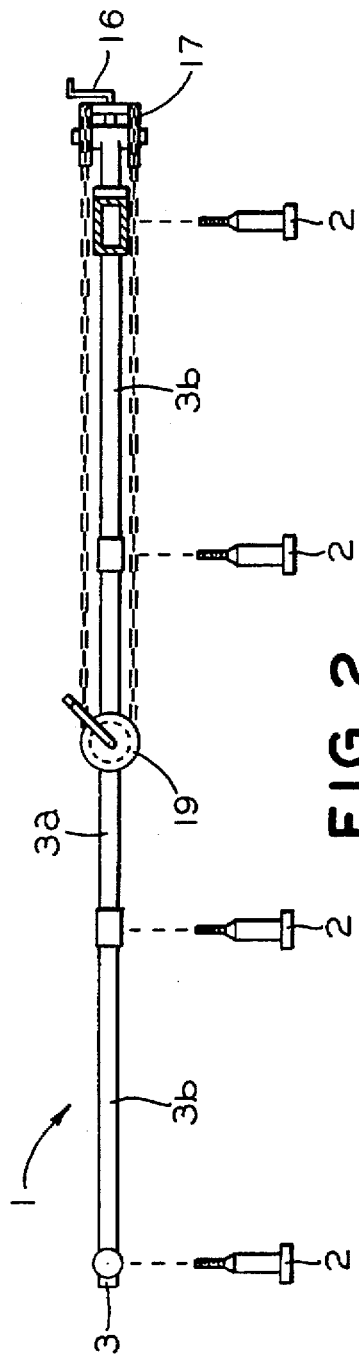

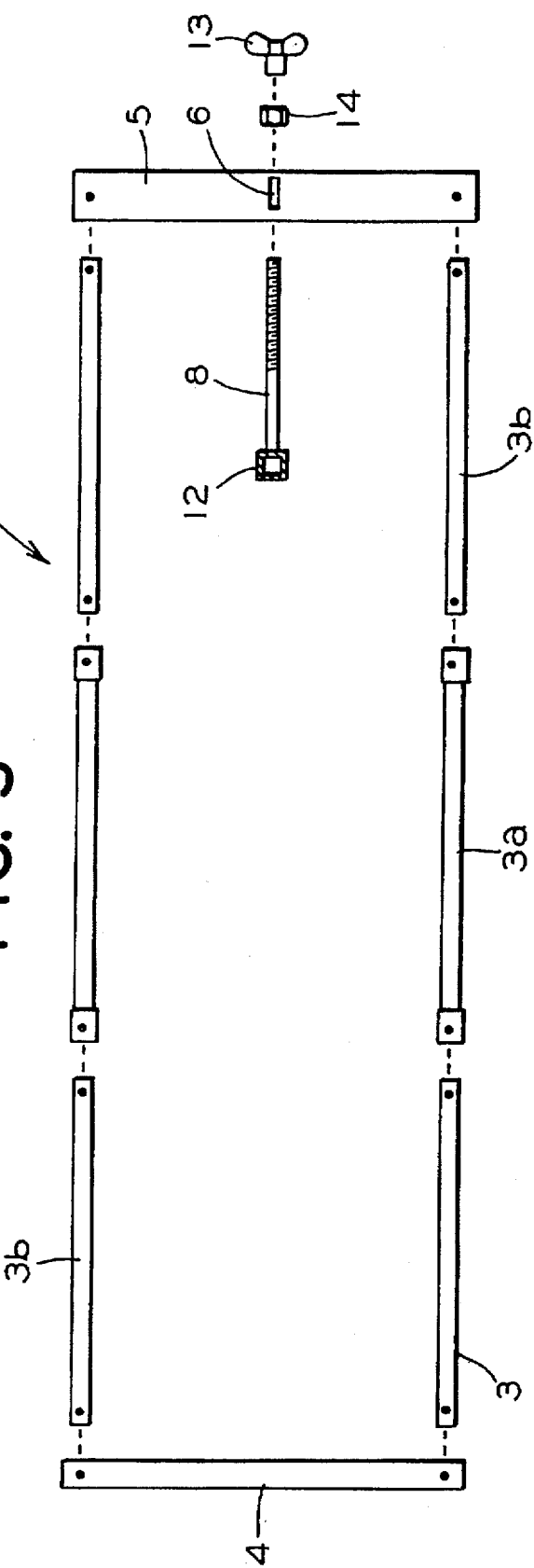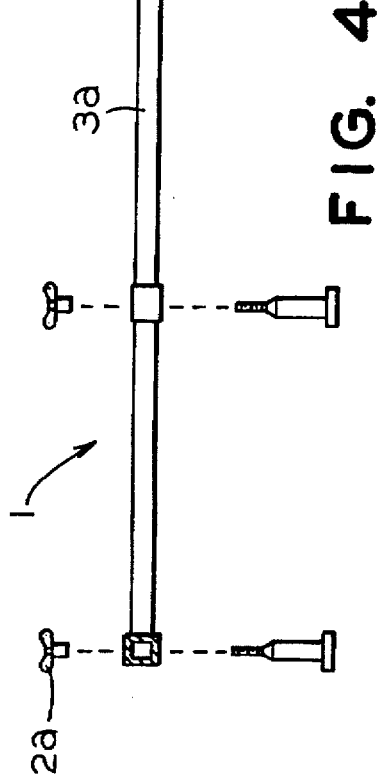

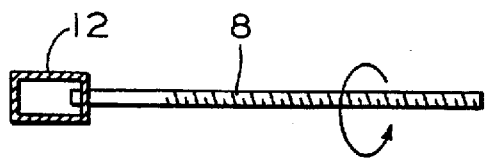
FIG. 5
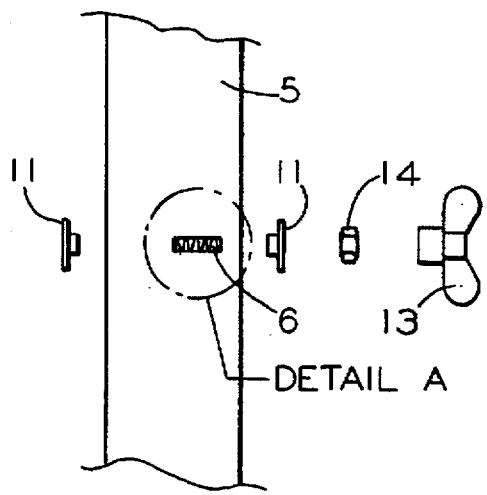
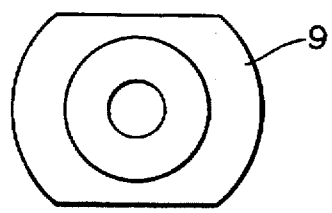
FIG. 7
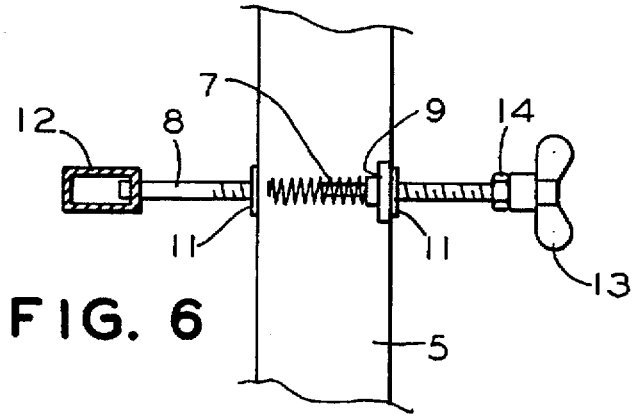
FIG. 6
FIG. 7A
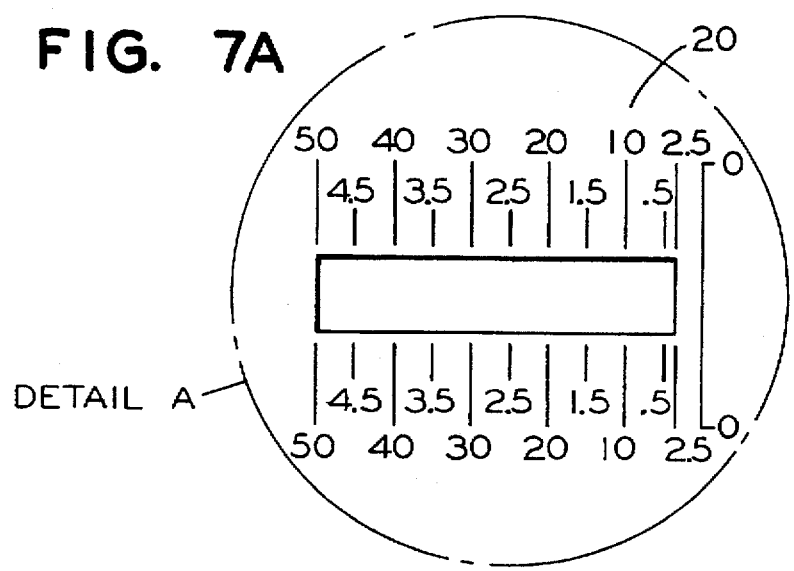
FIG. 8

5,895,367

1

MEDICAL THERAPEUTIC DEVICE FOR PLACING A PATIENT INTO EITHER TRACTION OR COMPRESSION

BACKGROUND OF THE INVENTION

The present invention relates to a new medical therapeutic device, and more particularly to a portable medical therapeutic device for placing various portions of a patient's body into either traction or compression, which device has a number of extraordinary advantages which includes not only an ability to effect either traction or compression, but such traction or compression can be applied to a number of different portions of the human body, such as compression on one or both legs, cervical traction, lumbar and thoracic traction and other such variations. Furthermore, the device can be utilized to effect such tension or compression while the patient is lying down at rest, and because of its portable nature, the device can be transported to a patient in need thereof lying on a bed, surgical table, x-ray table, massage table, floor, accident site or virtually anywhere a patient in need thereof may be located. In addition, the device can optionally include a dynamometer for measuring the applied traction or compressive forces.

It is well known by medical personnel, that application of traction or compression to portions of the human body may be therapeutically necessary or desired, during several differing medical procedures, such a providing protective measures during massage, treatment or exercise for muscle stimulation, surgical procedures, or merely to providing comfort and protection to accident victims or wounded persons.

Most prior art devices for placing patient into traction or compression, usually comprise a table onto which the patient is placed, and include attachments for supporting the patient at various points along the body, many of which are usually localized in the area of the armpits. Such tables can normally be place in an inclined position, so that the patient's own weight will cause him or her to hang by the armpits, causing tense muscles and overloading of the armpits, which is a rather delicate region of the human body. Other types of equipment are known wherein a lying patient is tied near the waist and neck area with tension applied by the patient's own foot motion.

Many forms of prior art equipment are capable of providing only one form of traction, so that it is not possible, for example, to accomplish cervical traction in combination with lumbar traction, or to effect compression. Another characteristic of most prior art equipment included the fact that it is not possible to measure the degree of tractive or compressive forces applied, which is most unfortunate in many exercises.

Still another prior art device is known wherein a lying patient is placed in traction at one end by harnessing the neck, while a cable, passing under the legs held in the air by a special device, acts along the pelvis. This type of equipment cannot accomplish compression, nor even tension in certain isolated parts of the human body. Here too, there is no way to measure the forces applied.

Common to almost all such prior art devices, is the fact that they are not portable, making it impractical or impossible to transport the device to the patient, thereby necessitating that the patient be transported to the location of the device, even in situations where such patient movement may not be medically advisable. In addition, such prior art devices are not normally self-sufficient, in that most normally require the use of special support, such as a bed with special features for installing and/or attaching the traction/compression equipment to the bed or a support structure adjacent to the bed.

SUMMARY OF THE INVENTION

This invention is predicated upon a new and improved medical therapeutic device for placing various portions of a patient's body into either traction or compression, which device is portable and can be taken to any location where such a patient may be located, not only having the ability to effect either traction or compression, but such traction or compression can be applied to a number of different portions of the human body. Furthermore, the device can be utilized to effect such tension or compression while the patient is lying down at rest, and because of its portable nature, the device can be transported to a patient in need thereof lying on a bed, surgical table, x-ray table, massage table, floor, accident site or virtually anywhere a patient in need thereof may be located. In addition, the inventive device can optionally include a dynamometer for measuring the applied traction or compressive forces.

OBJECTS OF THE INVENTION

It is a primary object of this invention to provide a new, improved and simple medical therapeutic device for placing various portions of a patient's body into either traction or compression.

Another object of this invention is to provide a new, improved and portable medical therapeutic device for placing various portions of a patient's body into either traction or compression.

A further object of this invention is to provide a new and improved medical therapeutic device for placing various portions of a patient's body into either traction or compression, which device is not only portable, but can be utilized on a patient lying on practically any generally horizontal surface.

Still another object of this invention is to provide a new and improved medical therapeutic device for placing various portions of a patient's body into either traction or compression, which device is not only portable, but provides an ability to select significant number of different body parts for application of such traction or compression.

An even further object of this invention is to provide a new, improved and portable medical therapeutic device for placing various portions of a patient's body into either traction or compression which device is capable of measuring traction or compression forced applied.

An additional object of this invention is to provide a new and improved cable driven automotive gear lever joint mechanism of simple construction which eliminates a commonly existing "telephone"; i.e., through cable transmitted vibrations of the vehicle engine.

Still an even further object of this invention is to provide a new and improved cable driven automotive gear lever joint mechanism of simple construction which permits attachment of a gear lever arm on the underside of the structure, as is necessary for some applications.

These and other objects and advantages will become apparent from a full understanding of the following detailed description when read with reference to the attached drawings.

BRIEF DESCRIPTION OF THE DRAWINGS

FIG. 1 is a plan view of a portable medical therapeutic device in accordance with a preferred embodiment of this invention illustrating the device as viewed from above when disposed in a horizontal position, further illustrating an optional patient operated control system.

FIG. 2 is a side view of the device illustrated in FIG. 1.

FIG. 3 is an exploded view of the apparatus shown in FIG. 1 illustrating the component parts of the rectangular frame in a spaced-apart relationship, with this embodiment not including the optional patient-operated system shown in FIGS. 1 and 2.

FIG. 4 is an elevational side view of the device illustrated in FIG. 3.

FIG. 5 is an exploded, schematic side view of the elongated post member showing the nature of its attachment to the transverse reaction foot member.

FIG. 6 is substantially the same as FIG. 5 except that the component parts are shown in an "as assembled" condition.

FIGS. 7 and 7a are respectively top and side views of the nut 9 shown in FIGS. 5 and 6.

FIG. 8 is a view of a graded scale of a dynamometer as may optionally be included in the apparatus of this invention.

DETAILED DESCRIPTION OF THE PREFERRED EMBODIMENTS

Figure 9:
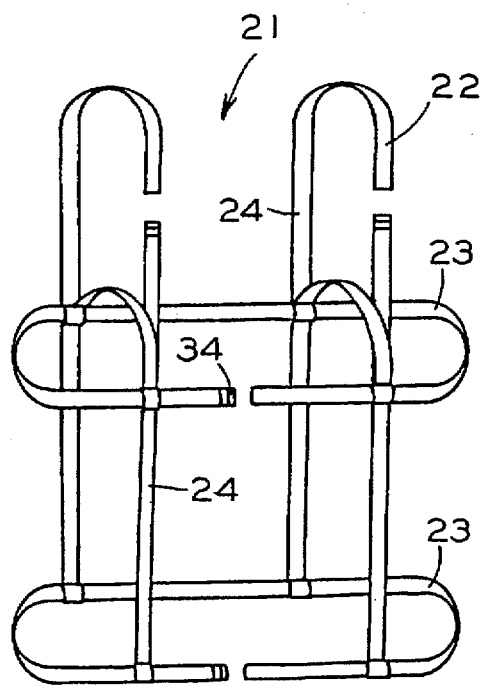
FIG. 9 is an isometric view of a vest type anchorage element as may be used in combination with the apparatus of this invention.

Pursuant to one presently preferred embodiment of the portable medical therapeutic device of this invention for placing various portions of a patient's body into either traction or compression, comprises a plurality of elongated structural elements, such as pipe elements, joinable together to form a rectangular frame 1. Specifically, as shown, elongated end pipe elements 3b are joined to each end of a central pipe element 3a. For example, pipe elements 3b can have a slightly smaller diameter than pipe elements 3a so that pipe elements 3b can be fitted into pipe elements 3a to form the elongated side portions of rectangular frame 1, which are maintained in a parallel relationship by a transverse reaction head member 4 at a first end, and a transverse reaction foot member 5 at a second end. While the transverse reaction head member 4, and transverse reaction foot member 5, can be tubular or of pipe form like the rest of the structural members of rectangular frame 1, they are preferably rectangular in cross-section as shown. Accordingly, the rectangular frame 1 comprises the generally parallel side portions comprising structural elements 3a and 3b, and the generally parallel transverse reaction head member 4 and transverse reaction foot member 5. By utilizing a rectangular form for transverse reaction foot member 5, it is possible to optionally incorporate a dynamometer therein, the graded scale 20 of which (FIG. 8) can be shown through rectangular aperture or viewfinder 6, in transverse reaction member 5.

A plurality of support feet members 2 are attachable to one side of rectangular frame 1, so that frame 1 can be supported on a horizontal surface, specifically, a horizontal surface upon which a patient to be treated, is lying. While any one of a number of different techniques can be utilized for attaching support feet members 2 to rectangular frame 1, FIG. 4 illustrates one technique whereby thumb-nuts 2a are attachable to threaded ends of the support feet members 2 extending through spaced apertures 3 in rectangular frame 1. Ideally, the spaced apertures 3 are provided through the couplings used to join the various components of rectangular frame 1.

Whether or not a dynamometer is included, transverse reaction foot member 5 is provided with an elongated post member 8, which can be drawn into transverse reaction foot member 5. Post member 8 extends parallel between the pair of elongated, generally parallel side portions of frame 1, having a first end inserted through the mid-point of transverse reaction foot member 5, and means provided for drawing post member 8 into transverse reaction foot member 5, such as, for example, as shown in FIGS. 3 and 4, a knob 13 and a nut 14 is threaded onto the end of post member 8, so that manual turning of nut 14 will pull post member 8 into transverse reaction foot member 5. In the central area of the transverse reaction foot member 5, a calibrated spring 7 is connected to a cylindrical part 9 with a central threaded hole 10 and washers 11. Preferably, as shown by the solid lines in FIGS. 1 and 2, a crank system 15 with a crank handle 16 is provided for drawing post member 8 into transverse reaction foot member 5. Such a crank system 15 can be provided directly on the threaded end of post member 8 for operation by a third person, such as a medical attendant. In the alternative, a second crank system 19 can be mounted on the side or the rectangular frame 1 with interconnecting cables to crank system 15 via pulleys 17 on support post 18, so that the device can be self-operated by the patient lying within frame 1. The opposite end of post member 8 is provided with an attaching means, such as ring 12, for attaching a first anchorage element 21 adapted to fasten a first selected body part of such patient to the means or ring 12. Accordingly, 27 must be provided which is adapted to fasten a second selected body part of such patient to the transverse reaction head member 4.

As is apparent from the above disclosure, the inventive portable medical therapeutic device is completed by including the first and second anchorage elements 21 and 27, each of which are adapted to respectively fasten first and second selected body parts of such patient to the rectangular frame 1. The first and second anchorage element 21 and 27 can be provided in any number of differing forms, depending upon which area of the human body are to be treated, and whether the treatment is to be traction or compression, as will be described below.

FIG. 9, for example, illustrates a vest type anchorage element 22 as may be used for lumbar traction, and comprises two parallel bands 23 of elliptical profiles, with adjustable fasteners 34 made of hook and loop material with a pair of transverse and parallel rectilinear ties 24.

Figure 10:
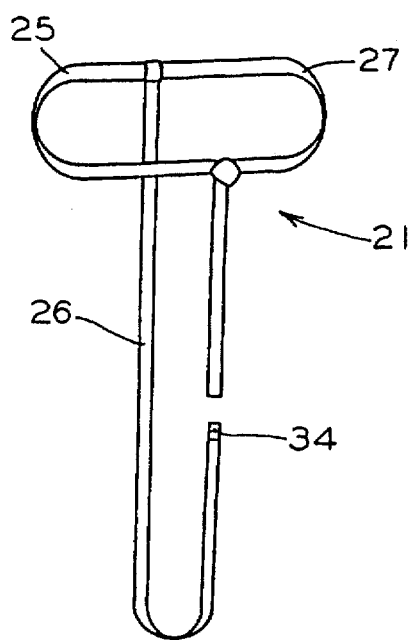
FIG. 10 is an isometric view of a belt type anchorage element as may be used in combination with the apparatus of this invention.

FIG. 10 illustrates a belt type anchorage element as may be used in either traction or compression, which includes a generally elliptical belt 25 and a tie 26.

Figure 11:
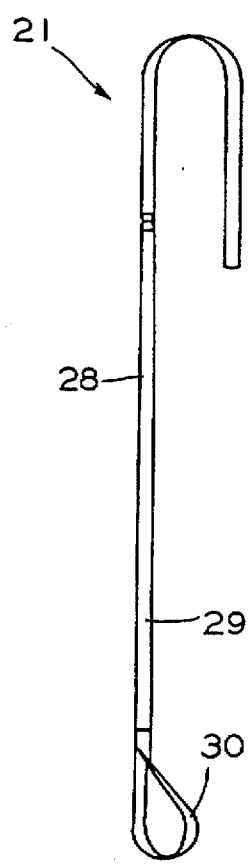
FIG. 11 is an isometric view of a stirrup type anchorage element as may be used in combination with the apparatus of this invention.

FIG. 11 illustrates a stirrup type anchorage element as may be used in combination with the apparatus of this invention, and comprises a stirrup loop 30 at the end of an elongated 28-29.

Figure 12:
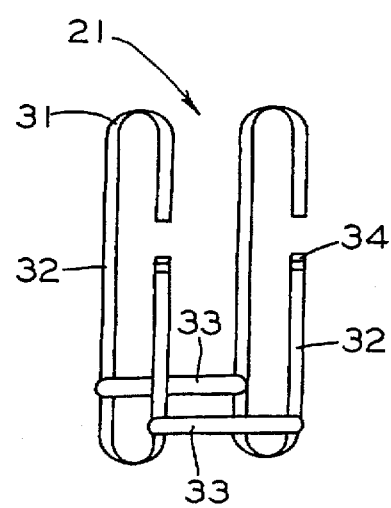
FIG. 12 is an isometric view of a neck harness type anchorage element as may be used in combination with the apparatus of this invention.

FIG. 12 is an isometric view of a neck harness type anchorage element as may be used in combination with the apparatus of this invention, and comprises two parallel ties 32 joined by a pair of parallel bands 33.

Figure 13:
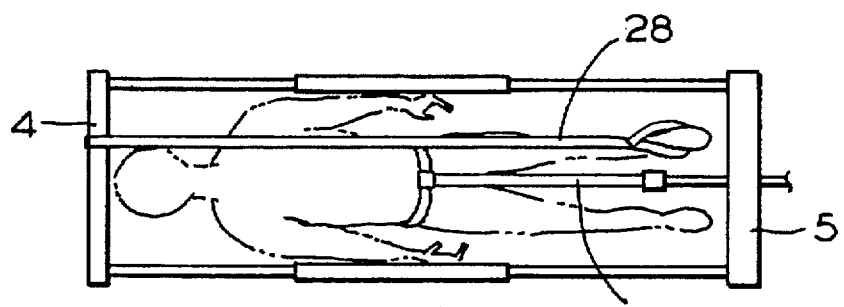
FIG. 13 is an isometric view of a leg compression type anchorage element as may be used in combination with the apparatus of this invention.
Figure 14:
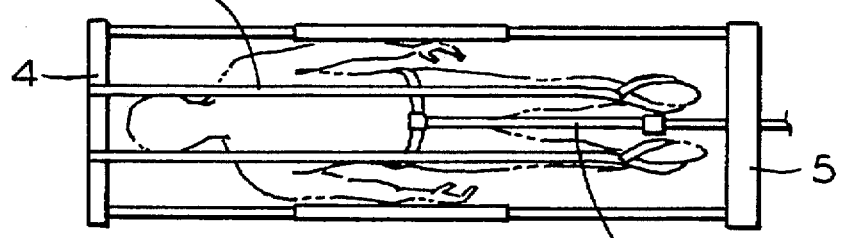
FIG. 14 is an isometric view of a two leg compression type anchorage element as may be used in combination with the apparatus of this invention.
Figure 15:
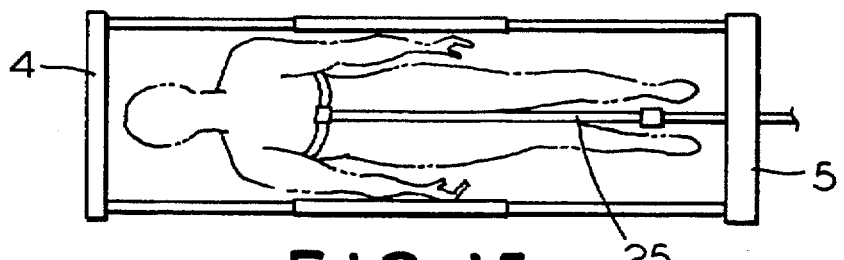
FIG. 15 is an isometric view of a cervical traction type anchorage element as may be used in combination with the apparatus of this invention.
Figure 16:
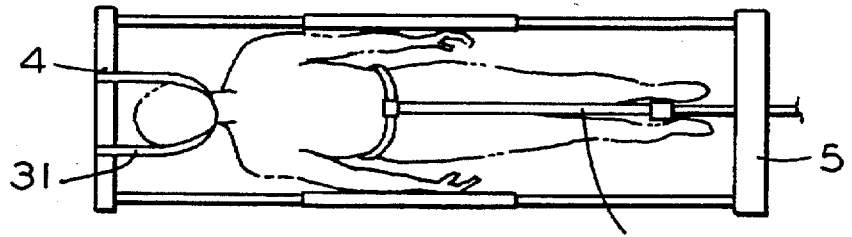
FIG. 16 is an isometric view of a lumbar thoracic and cervical traction type anchorage element as may be used in combination with the apparatus of this invention.
Figure 17:
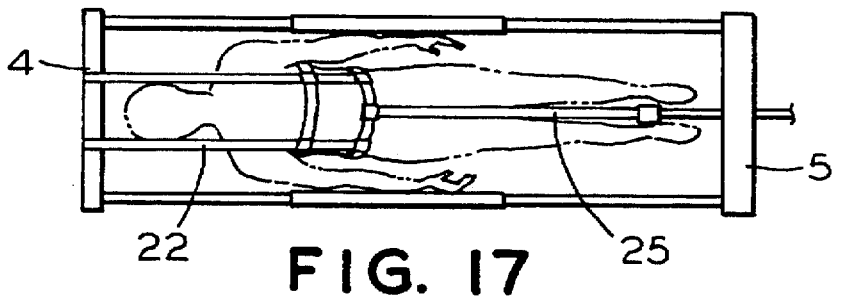
FIG. 17 is an isometric view of a lumbar traction type anchorage element as may be used in combination with the apparatus of this invention.

FIGS. 13–17 are each a plan view of the rectangular frame 1 further illustrating how various types of anchorage elements can be secured thereto to treat various portions of a patients body. For example, FIG. 13 illustrated how a single leg of a patient can be placed in tension by utilizing in combination a belt type anchorage element of FIG. 10 and a stirrup type anchorage element of FIG. 11. FIG. 14 is substantially the same as FIG. 13, except that two stirrup anchorage elements are utilized, one for each leg. FIG. 15 shows how cervical traction can be effected by utilizing a simple head harness in combination with a belt type anchorage element secured under the arms of the patient. FIGS. 16 and 17, illustrate two different ways for placing the patient's back in traction utilizing a belt type anchorage element of FIG. 10 in combination with either simple head harness to effect either lumbar thoracic and cervical traction (FIG. 16), or to effect just lumbar traction with a vest type anchorage element substituted for the head harness (FIG. 17).

As can be seen from the above detailed disclosure, this invention provides a new medical therapeutic device for placing various portions of a patient's body into either traction or compression, by either an attendant or even the patient him or her self. The device can easily be assemble or disassemble and packed is a convenient pack, thereby making it portable so that it can be easily transported to a patient's location or even carried in an ambulance. As should also be clear from the above disclosure, the device of this invention can be utilized on a patient lying in any position, i.e., on his back, stomach, left side or right side, without applying force to the area of the patient's armpits, and therefore can be utilized to apply such traction of compression for relatively long periods of time, while permitting the patient to remain relaxed and in the absence of pain.

I claim:

1. A portable, medical therapeutic device for placing a patent, lying on a generally horizontal surface, into traction or compression, said device comprising;

(a) a plurality of elongated structural members capable of being joined together to form a rectangular frame, said rectangular frame having a pair of elongated, generally parallel side portions with first ends thereof spaced by a transverse reaction head member, and second ends thereof spaced by a transverse reaction foot member;

(b) a plurality of support feet members attachable to one side of said rectangular frame, such that said plurality of support feet members will horizontally support said rectangular frame on such generally horizontal surface upon which such a patient is lying, such that said rectangular frame will be horizontally disposed around such patient;

(c) an elongated post member extending parallel between said pair of elongated, generally parallel side portions, said elongated post member having a first end attached to a mid-point of said transverse reaction foot member, with a ring attached at a second end thereof, said post member having a length adapted to extend in a generally parallel relationship between the legs of such patient;

(d) a first anchorage element adapted to fasten a first selected body part of such patient and connected to said ring on said elongated post member;

(e) a second anchorage element, adapted to fasten a second selected body part of such patient and connected to said transverse reaction head member; and (f) means for mechanically drawing said post member into said transverse reaction foot member such that said ring on said elongated post member is forcibly moved generally horizontally away from said transverse reaction head member.

* * * * *